United States Patent

Tadano et al.

[11] Patent Number: 5,840,512
[45] Date of Patent: Nov. 24, 1998

[54] METHOD FOR MEASUREMENT OF IONIZED CALCIUM

[75] Inventors: Toshio Tadano; Akira Miike, both of Shizuoka; Norihiko Kayahara, Kanagawa; Jun Umemoto, Hyogo, all of Japan

[73] Assignee: Kyowa Medex Co., Ltd., Tokyo, Japan

[21] Appl. No.: 553,512

[22] PCT Filed: May 30, 1994

[86] PCT No.: PCT/JP94/00851

§ 371 Date: Apr. 3, 1996

§ 102(e) Date: Apr. 3, 1996

[87] PCT Pub. No.: WO94/28167

PCT Pub. Date: Dec. 8, 1994

[30] Foreign Application Priority Data

May 31, 1993 [JP] Japan ................................. 5-129379

[51] Int. Cl.[6] ............................ C12Q 1/34; C12Q 1/00; H01L 21/302
[52] U.S. Cl. .................. 435/18; 435/4; 435/967; 436/79; 436/74; 424/94.1; 424/94.6; 544/358; 252/374
[58] Field of Search .................... 435/18, 4, 967; 436/79, 74; 424/94.1, 94.6; 544/358; 252/374

[56] References Cited

U.S. PATENT DOCUMENTS

| 4,761,369 | 8/1988 | Steinman | 435/19 |
| 4,806,486 | 2/1989 | Sprokholt et al. | 435/19 |
| 5,384,247 | 1/1995 | Berry et al. | 435/22 |

FOREIGN PATENT DOCUMENTS 4023999  1/1992  Japan.

OTHER PUBLICATIONS

Stryer, "Biochemistry", p. 39, 1975. Month not available.

*Primary Examiner*—Louise Leary
*Attorney, Agent, or Firm*—Fitzpatrick, Cella, Harper & Scinto

[57] ABSTRACT

The present invention relates to a method for quantitatively determining ionized calcium in a sample by using a phospholipase, which comprises carrying out an enzyme reaction with the phospholipase in a buffer comprising a nitrogen heterocycle-binding sulfonic acid having a pK ranging 6.6 to 7.6 or a salt thereof.

According to the method of the invention, the amount of ionized calcium in a sample, such as serum, can be accurately determined.

2 Claims, 1 Drawing Sheet

METHOD FOR MEASUREMENT OF IONIZED CALCIUM

TECHNICAL FIELD

This invention relates to a method for measuring ionized calcium by using an enzyme.

BACKGROUND ART

Calcium contained in blood can be classified into the three kinds of protein-binding calcium, complexing calcium and ionized calcium. Among these, only ionized calcium is important in clinical tests and the amount of ionized calcium in blood is measured in a test for parathyroid functions, a cardiac operation and the like. As a method for selectively determining the amount of ionized calcium, the ion electrode method is known. However, this method requires much time for operation and cannot treat a large number of samples at one time. Therefore, it is not suitable for clinical tests.

As a method for treating a large number of samples at one time, there have been disclosed a method for quantitatively determining calcium by using a phospholipid, phospholipase D and N-tris(hydroxymethyl)methyl-2-aminoethanesulfonic acid [TES] buffer (Japanese Unexamined Patent Publication No. 62-195297 and EP486997A); a method for quantitatively determining calcium by using phosphorylcholine thioester, phospholipase $A_2$ and Tris-maleic acid buffer (Japanese Unexamined Patent Publication No. 1-231896); a quantitative determination method by using calmodulin (Japanese Unexamined Patent Publication No. 62-36199); and a quantitative determination method by using pyruvate kinase (Japanese Unexamined Patent Publication No. 2-142498). However, selective determination of ionized calcium is impossible by these methods.

DISCLOSURE OF THE INVENTION

It is an object of the present invention to provide a method by which a large number of samples can be treated at one time and, at the same time, the amount of ionized calcium in a sample can be determined selectively.

The method of the present invention for measuring ionized calcium belongs to a method for quantitatively determining calcium in a sample by using a phospholipase. The present method is characterized in that an enzyme reaction with the phospholipase is carried out in a buffer comprising a nitrogen heterocycle-binding sulfonic acid having a pK ranging from 6.6 to 7.6 or a salt thereof.

As a sample containing calcium, any sample may be used as long as it is miscible with the buffer. A preferable sample is a biosample such as plasma, cell extract and the like.

In the present invention, "phospholipase" means a general term for those enzymes which hydrolyze a phospholipid and a partial hydrolysate thereof. Examples of phospholipase include phospholipase $A_1$ [EC 3.1.1.32], phospholipase $A_2$ [EC 3.1.1.4] and phospholipase D [EC 3.1.4.41].

As a method for quantitatively determining calcium by using a phopholipase, the following methods are illustrated. There are a method wherein phospholipase $A_1$ or $A_2$ and a substrate thereof are used. In these methods, the amount of calcium in a sample is determined by measuring activity of phospholipase $A_1$ or $A_2$ (Japanese Unexamined Patent Publication No. 1-231896). Furthermore, there is a method wherein phospholipase D and a substrate thereof are used. In this method, the amount of calcium in a sample is determined by measuring phospholipase D activity (Japanese Unexamined Patent Publication No. 62-195297 and EP486997A); and the like.

As a substrate for phospholipase $A_1$ or $A_2$, phosphatidylcholine, phosphatidylglycerol, phosphatidylethanolamine and the like are enumerated. As a substrate for phospholipase D, phosphatidylcholine, phosphatidylglycerol, phosphatidylethanolamine, phosphatidylinositol, phosphatidylserine and the like are enumerated.

As a reaction product of phospholipase $A_1$ or $A_2$, acetic acid, fatty acid (monocarboxylic acid) and the like are enumerated. As a reaction product of phospholipase D, choline, glycerol, ethanolamine, inositol, serine and the like are enumerated.

As a method for determining the amount of a reaction product of phospholipase $A_1$ or $A_2$, there are a method which comprises reacting acetic acid with a dehydrogenase such as alcohol dehydrogenase in the presence of reduced nicotinamide adenine dinucleotide (NADH) or the like [J. Biol. Chem., 247:267 (1972)]; a method which comprises the following steps, adding phosphoenolpyruvic acid to adenosine diphosphate (ADP) produced by an acetate kinase reaction between acetic acid and adenosine triphosphate (ATP) as a substrate to thereby produce pyruvic acid by a pyruvate kinase reaction, adding NADH to the resultant pyruvic acid and measuring the amount of NADH which decreases by a lactate dehydrogenase reaction [J. Biochem., 84: 193 (1978)]; a method which comprises the following steps, reacting fatty acid with acyl CoA synthetase in the presence of coenzyme A (CoA) and ATP, converting the resultant adenosine monophosphate (AMP) into lactic acid by an enzyme chain reaction using adenylate kinase and pyruvate kinase, reacting the resultant lactic acid with lactate dehydrogenase and measuring the amount of NADH which decreases by the lactate dehydrogenase reaction [Eur. J. Biochem., 93:197 (1979)]; and the like.

As a method for determining the amount of a reaction product of phospholipase D, there are a method which comprises converting glycerol into glyceraldehyde by using glycerol oxidase and measuring the amount of the resultant hydrogen peroxide [Agr. Biol. Chem., 44:399 (1980)]; a method which comprises converting glycerol into glycerol-3-phosphoric acid by using ATP and glycerol kinase and measuring the amount of NADH produced by a subsequent glyceroptiosphate dehydrogenase reaction [J. Biol. Chem., 242:1030 (1967)]; a method which comprises decomposing ethanolamine into glyceraldehyde, ammonia and hydrogen peroxide by using ethanolamine oxidase and quantitatively determining these substances [J. Biol. Chem., 239:2189 (1964)]; a method which comprises reacting inositol with myo-inositol lehydrogenase in the presence of NAD and measuring the resultant NADH [Arch. Biochem. Biophys., 60:352 (1956)]; a method which comprises converting serine into pyruvic acid and ammonia by using serine dehydrogenase and quantitatively determining the reaction product [Methods Enzymol., 178:346 (1971)]; a method which comprises converting choline into betaine by a choline oxidase reaction and quantitatively determining the resultant hydrogen peroxide [Japanese Unexamined Patent Publication No. 62-195297]; and the like. As a method for quantitatively determining hydrogen peroxide, there is a colorimetric method comprising measuring quinone-type dyestuff produced by a peroxidase reaction in the presence of N-ethyl-N-(3-methylphenyl)-N'-acetylethylenediamine (EMAE) or a phenol and an antipyrine such as 4-aminoantipyrine [SHIN-RINSHOUKENSAGISHI-KOHZA (New Course for Clinical Technicians), Vol. 9

(Clinical Chemistry), Igaku Shoin Co. (1986)]. As a method for quantitatively determining glycerol-3-phosphoric acid, there is a method comprising reducing glycerol-3-phosphoric acid by using glycerophosphate dehydrogenase in the presence of NAD and measuring the amount of NADH converted from NAD.

As a nitrogen heterocycle-binding sulfonic acid having a pK ranging from 6.6 to 7.6, N-2-hydroxyethlylpiperazine-N'-2-ethanesulfonic acid [HEPES], 3-(N-morpholino) propanesulfonic acid [MOPS], piperazine-N,N'-bis(2-ethanesulfonic acid) [PIPES], 1,2-N,N'bis(N",N'"-di(2-sulfoethyl)piperazino)ethane [Bis-PIPES] and the like may be enumerated. As a salt thereof, a sodium salt, potassium salt or lithium salt thereof and the like may he enumerated.

Now, preferred embodiments of the method of the invention for measuring ionized calcium will be described hereinbelow. A buffer comprising a nitrogen heterocycle-binding sulfonic acid having a pK ranging from 6.6 to 7.6 or a salt thereof (10–150 mM) is adjusted so that it has a pH ranging from 6.6 to 7.6, preferably 7.4, at 37° C. To this buffer, sodium chloride, potassium chloride or the like is added as an ionic strength modifier to give a concentration of 0–100 mM in the reaction solution. A phospholipase is added thereto (1–20 U/ml reaction solution) and those reagents necessary for quantitative determination of a phospholipase reaction, such as choline oxidase (1–20 U/ml reaction solution) and EMAE (0.2–1 mg/ml reaction solution), are added further. The resultant solution is incubated at 37° C. Then, a sample is added to this solution to thereby produce reaction products. The amounts of the reaction products obtained are measured by the methods for quantitatively determining the reaction products of phopholipase reactions described above.

When substances such as endogenous hydrogen peroxide, an endogenous phospholipid which is a substrate for a phospholipase to be used, a substance susceptible to oxidation, substrates for various enzymes to be used for quantitative determination of reaction products and the like may be present in a sample to be used in the present invention, and these substances may interfere with the measurement, a pretreatment of a sample can be carried out by adding the following compounds to the sample. The compounds include enzymes such as catalase, phospholipase, lysophospholipase and the like to be used for the quantitative determination of reaction products and an oxidant such as potassium ferricyanide, ascorbate oxiclase or the like, to thereby eliminate the interfering substances.

Further, an excipient such as lactose, a solubilizer such as sodium cholate and Dispanol TOC (commercial name), a corresponding amount of calcium chloride for supplementing an extremely small amount of calcium which binds to reagents, and the like may be added to the reaction solution provided that these substances would not influence upon the determination reaction.

BRIEF DESCRIPTION OF THE DRAWINGS

In FIG. 1, marks -●- and -○- represent a calibration curve in a standard solution with addition of albumin and a calibration curve in a standard solution without addition of albumin, respectively.

BEST MODE FOR CARRYING OUT THE INVENTION

Figure 1:
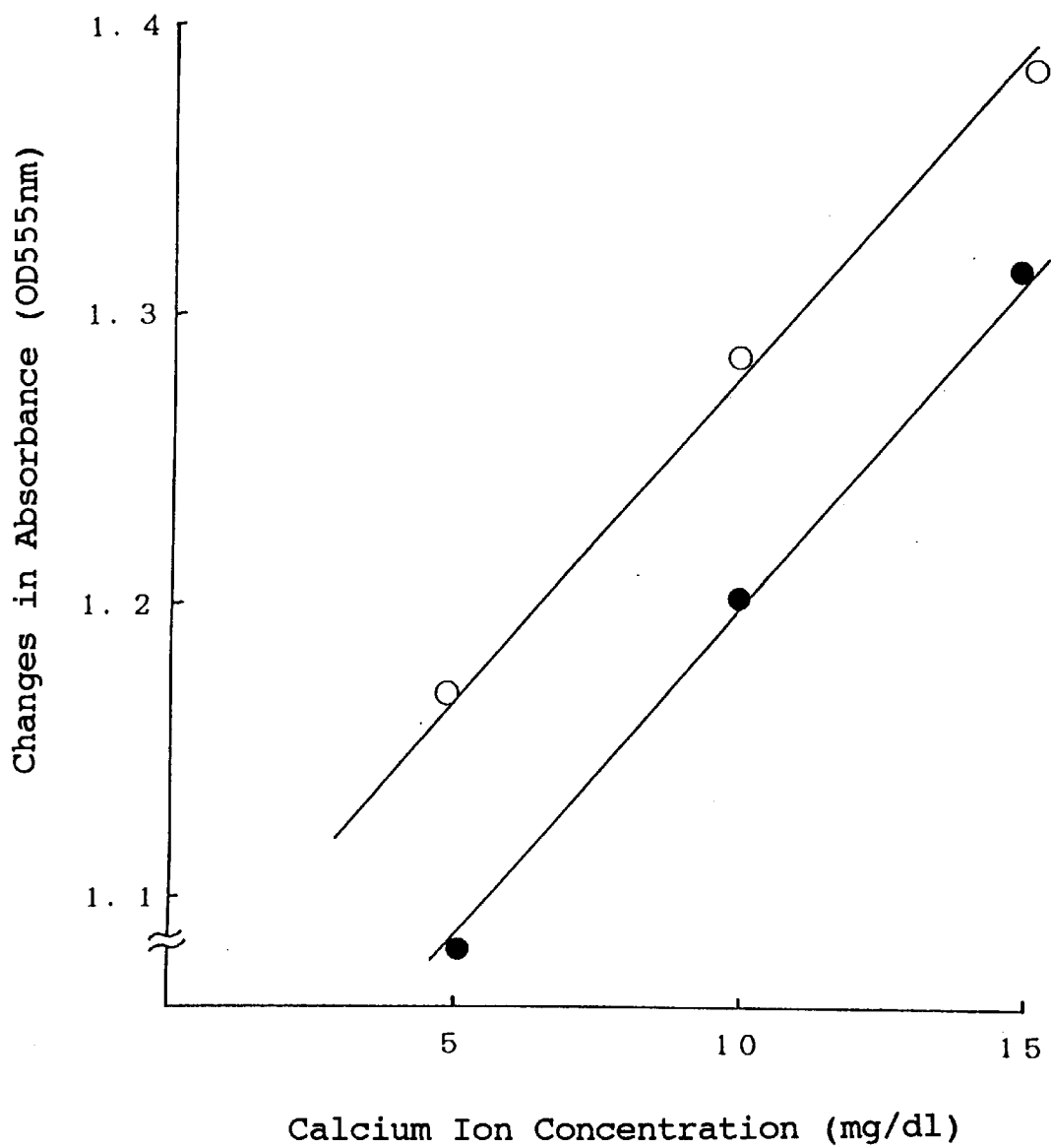
FIG. 1 is a graph showing calibration curves; obtained by using HEPES buffer.

The present invention will be described in more detail hereinbelow with reference to the following examples and comparative example, which should not be construed as limiting the technical scope of the present invention.

(EXAMPLE 1)

(1) Preparation of the First Reagent

To 180 ml of 50 mM HEPES buffer (pH 7.4, 37° C.), lactose (1.38 mg/ml reaction solution), EMSE (0.7 mg/ml reaction solution), phospholipase D (4 U/ml reaction solution), catalase (400 U/ml reaction solution), ascorbate oxidase (3 U/ml reaction solution) and Dispanol TOC (product name) (0.2% in reaction solution) were added to prepare the first reagent.

(2) Preparation of a Color Forming Agent

To 70 ml of 50 mM HEPES buffer (pH 7.4, 37° C.), lactose (4.3 mg/ml reaction solution), 4-aminoantipyrine (1.3 mg/ml reaction solution), acetylphosphatidylcholine (2.7 mM in reaction solution), choline oxidase (1 U/ml reaction solution) and peroxidase (39 U/ml reaction solution) were added to prepare a color forming agent.

(3) Preparation of Standard Solutions

Calcium chloride was diluted with distilled water to give concentrations of 5 mg/dl, 10mg/dl and 15 mg/dl in the reaction solution, to thereby obtain standard solutions. In order to prepare the standard solution to be the same condition as the serum, in which the amount of ionized calcium and the total amount of calcium are different, another type of standard solutions were also prepared by adding albumin (5 g/dl reaction solution).

(4) Measurement

To 2.5 ml of the first reagent incubated at 37° C. in a cell mounted in a spectrophotometer, 0.01 ml of a sample or the standard solution was added and mixed at 37° C. for 5 minutes. Then, 0.5 ml of the color forming agent was added and mixed. The measurement of absorbance at 555 nm was started 20 seconds after the mixing and continued thereafter. Changes in absorbance from 1 to 3 minutes from the start of the measurement were determined. Calibration curves in a standard solution with addition of albumin and a standard solution without addition of albumin were prepared. The calibration curves thus obtained are shown in FIG. 1.

According to FIG. 1, the gradient of a calibration curve in a standard solution with addition of albumin (the amount of ionized calcium < the total amount of calcium) is equal to the gradient of a calibration curve in a standard solution without addition of albumin (the amount of ionized calcium = the total amount of calcium). In addition, the absorbance in the albumin-added standard solution is smaller. Therefore, it has been demonstrated that the amount of ionized calcium can be measured by the method of the present invention.

(EXAMPLE 2)

Measurement of Serum Samples

Two serum samples, A and B, were used as samples. For each sample, total calcium concentration and ionized calcium concentration were measured by the ion electrode method (using the ionized calcium electrode ICA2 manufactured by Radiometer) in advance. As a result, total calcium concentration and ionized calcium concentration were 10. 5 mg/dl and 5.1 mg/dl, respectively, for A and 12.5 mg/dl and 5.9 mg/dl, respectively, for B. Ionized calcium concentrations were measured in these samples as described in Example 1. As a result, the ionized calcium concentration of A was 5.5 mg,/dl and that of B was 6.6 mg/dl.

(EXAMPLE 3)

Measurement by using MOPS Buffer

The two serum samples A and B were measured for ionized calcium concentration in the same manner as described in Example 1 except that MOPS was used instead of HEPES. As a result, the ionized calcium concentration of A was 5.3 mg/dl and that of B was 6.2 mg/dl.

(Comparative Example 1)

Measurement by using N-Tris(Hydroxymethyl) Methyl-2-Aminoethanesulfonic Acid [TES] Buffer The two serum samples A and B were measured for ionized calcium concentration in the same manner as described in Example 1 except that TES which is used in the method disclosed in EP486997A was used instead of HEPES. As a result, the ionized calcium concentration of A was 4.1 mg/dl and that of B was 9.4 mg/dl.

According to the measurement results obtained in Examples 2 and 3 and Comparative Example 1, it is clear that the amount of ionized calcium can be measured accurately only by the method of the present invention.

INDUSTRIAL APPLICABILITY

According to the present invention, there is provided a method for measuring ionized calcium which enables accurate quantitative determination of ionized calcium in a sample such as serum.

We claim:

1. A method for quantitatively determining ionized calcium, which comprises the steps of:

selecting a sample;

carrying out an enzyme reaction with a phospholipase in a buffer comprising a nitrogen heterocycle-binding sulfonic acid selected from the group consisting of N-2-hydroxyethylpiperazine-N'-2-ethanesulfonic acid, 3-(N-morpholino) propanesulfonic acid, 1,2-N, N'-bis (N",N'"-di(2-sulfoethyl)piperazino)ethane, and a salt thereof;

quantitatively determining a reaction product of said enzyme reaction; and correlating an amount of said reaction product with an amount of ionized calcium in said sample.

2. The method of claim 1 wherein the nitrogen heterocycle-binding sulfonic acid is N-2-hydroxyethylpiperazine-N'-2-ethanesulfonic acid, 3-(N-morpholino) propanesulfonic acid, or a salt thereof.

* * * * *